United States Patent [19]

Zimmerschied

[11] 4,228,307
[45] Oct. 14, 1980

[54] REMOVAL OF BROMINE FROM ACETIC ACID

[75] Inventor: Wilford J. Zimmerschied, Naperville, Ill.

[73] Assignee: Standard Oil Company (Indiana), Chicago, Ill.

[21] Appl. No.: 970,226

[22] Filed: Dec. 18, 1978

[51] Int. Cl.$^2$ .................... C07C 51/42; C07C 53/08; B01J 1/22; B01J 8/02
[52] U.S. Cl. .................................. 562/608; 562/414; 562/549
[58] Field of Search ............... 562/608, 606, 414, 549

[56] References Cited

U.S. PATENT DOCUMENTS

| 2,884,451 | 4/1959 | Graham | 562/608 |
| 3,084,109 | 4/1963 | Ure et al. | 562/608 |

Primary Examiner—Vivian Garner
Attorney, Agent, or Firm—Fred R. Ahlers; William T. McClain; William H. Magidson

[57] ABSTRACT

Acetic acid of 95 to 100 weight percent strength containing ionic and coordinate bromide impurities can be purified to a bromine content of less than 3 ppm by the sequence of steps comprising catalytic hydrogenating said acetic acid, treating the hydrogenated acetic acid with a solid absorbant and separating acetic acid therefrom.

5 Claims, No Drawings

REMOVAL OF BROMINE FROM ACETIC ACID

FIELD OF THE INVENTION

This invention relates to the removal of bromine from acetic acid and more specifically pertains to the removal of bromine from acetic acid obtained by the catalytic liquid phase oxidation of butane in the presence of catalysis provided by a combination of a source of bromine with one or more transition metal oxidation catalysts, more specifically cobalt, manganese or cobalt and manganese.

PRIOR ART BACKGROUND

According to the U.S. Pat. No. 3,293,292 it is essential for the preparation of acetic acid to use both manganese and cobalt (e.g., in their 2+ form acetate tetrahydrates) with a source of bromine (e.g., ammonium bromide) to oxidize butane with oxygen gas in the liquid phase at 176°–177° C. and a gauge pressure of 65.4 kg/cm² in the presence of acetic acid as reaction solvent.

More recently U.S. Pat. No. 4,111,986 discloses that acetic acid can be prepared by contacting a sufficient concentration of oxygen-containing gas (e.g., oxygen gas at at least 5 liters per hour per 100 grams of butane) with normal liquid butane in the presence of an acetic acid solution of components of catalysis consisting essentially of cobalt (e.g., 1 to 50 milliequivalents per mole of butane) and bromine (2 to 500 milliequivalents per mole of butane). For this process reaction temperatures of at least 176°–177° C. are preferred at gauge pressures of from 35 up to 211 kg/cm², preferably from 56 up to 105.5 kg/cm².

Concentrated acetic acid (even glacial) distilled from the effluent produced by the foregoing liquid phase oxidation processes is contaminated with bromine-containing compounds and is not generally suitable as an article of commerce even though the commercial specification for glacial acetic acid or acetic anhydride do not set a maximum allowable value for bromine concentration.

Also acetic acid becomes contaminated with bromides when used as solvent or reaction medium for the liquid phase oxidation of alkyl-substituted aromatic compounds (e.g., xylenes, toluene, trimethyl benzenes) with air to the corresponding aromatic carboxylic acids in the presence of catalysis provided by the components comprising a combination of one or more transition metal oxidation metal catalyst and a source of bromine (e.g., $Br_2$, HBr, inorganic bromide salt, organic bromide such as tetrabromoethane). While some who practice such process for the production of aromatic carboxylic acids reuse the bromine-contaminated acetic acid in the oxidation process, others (e.g., the assignee of U.S. Pat. No. 3,578,706) prefer to remove the bromine or bromine-containing contaminants before resuing the acetic acid in the oxidation process.

According to said U.S. Pat. No. 3,578,706, the bromine contaminated acetic acid is treated by reaction with a metal having electrochemical potential between manganese and iron, inclusive and then contacting the acetic acid through an anion exchanger to remove the bromine or bromides.

Such bromine contaminated acetic acids can contain both ionic and coordinate forms (e.g., bromine attached to carbon) of bromine which are not entirely removed by distillation or fractionation but rather carry through to the 97–100% acetic acid fraction in amounts of from 0.0005 up to 0.015 weight percent total of said two forms of bromine. We have found that by a single two step process the concentrated acetic acid can be purified to a bromine content below the present analytical detectability which is, on a weight basis, 3 parts bromine per $1 \times 10^6$ parts (i.e., 3 ppm) acetic acid.

STATEMENT OF THE INVENTION

The foregoing removal of bromine to a concentration of less than 3 ppm bromine by weight on acetic acid can be accomplished by (a) contacting the concentrated (95 to 100%) acetic acid containing from 0.0005 up to 0.015 weight percent bromine and hydrogen gas with a palladium catalyst, preferably a palladium catalyst having palladium crystallites dispersed on the surface of activated carbon; and (b) then contacting the concentrated acetic acid with a solid absorbant.

Such palladium on activated carbon ("Pd/C") catalyst can have, on a weight basis, from 0.01 up to 1.0 percent palladium. The activated carbon should have a high surface area per unit of mass, desirably at least 800 m²/g and preferably 1000 to 3000 m²/g and a low extraneous metal content.

The solid absorbant, for example can be any one of the low metal content activated carbons or alumina.

The step of contacting the bromine contaminated concentrated acetic acid and hydrogen with the Pd/C catalyst can be conducted with acetic acid in the liquid phase at a temperature of at least 50° C. or under vapor phase conditions at a temperature of at least 115° C. The liquid phase process is conducted by adding Br-contaminated concentrated acetic acid, particulate catalyst (2 to 20 mesh U.S. Standard Sieve) and hydrogen to a closed, pressure controlled vessel stirred zone at a temperature of from 50 up to 120° C. wherein the hydrogen partial pressure of from 0.35 up to 7 kg/cm² which will, at temperatures above 115° C., maintain the acetic acid in the liquid phase. The hydrogen-treated acetic acid can be withdrawn by decantation leaving the Pd/C catalyst in the reaction vessel or the suspension of Pd/C can be withdrawn through a filter. The liquid phase contacting also can be conducted by flow of acetic acid upward or downward through a fixed bed of Pd/C catalyst together with a hydrogen gas flow concurrent with or countercurrent to the flow of acetic acid through the fixed bed of Pd/C catalyst.

The vapor phase contact of acetic acid and hydrogen with Pd/C catalyst can be conducted by mixing hydrogen gas at a partial pressure of 0.35 to 7 kg/cm² and vaporized (115° to 125° C.) concentrated acetic contaminated with bromine and passing the vapor-gas mixture upward or downward through a bed of Pd/C catalyst.

The contacting of concentrated acetic acid with the solid absorbent can also be conducted with the acetic acid in the liquid or in the vapor phase. The liquid phase contacting with the solid absorbant can be carried out at a temperature of from about 20° up to 115° C. at 0 kg/cm gauge pressure or at a higher temperature and under elevated pressure to maintain acetic acid in the liquid phase. Such liquid phase contacting can be accomplished by a flow process wherein the liquid acetic acid is permitted to flow downward or upward through a fixed bed of particulated solid absorbant. Or the liquid acetic acid can be stirred with particulated solid absorbant and then separated by decantation, filtration, centrifugation or other means for solid-liquid separation.

A single lot of bromine contaminated concentrated acetic acid (99 wt. % acetic acid) containing 58 ppm total of ionic and coordinate bromine is used in the following 5 examples, two of which are illustrative of the best mode of contact presently contemplated for the practice of the present invention.

COMPARATIVE EXAMPLE I

Ten milliliters of the 58 ppm bromine contaminated bromine is percolated through 1.0 gram of activated alumina at a temperature between 20° and 22° C. By X-ray diffraction analysis the acetic acid recovered is found to contain 54 ppm total of ionic and coordinate bromine.

COMPARATIVE EXAMPLE II

Ten milliliters of the 58 ppm bromine contaminated concentrated acetic acid are percolated through 1.0 gram of activated carbon of low metal content, i.e., 0.65 weight percent total metals. The recovered acetic acid is found by X-ray diffraction analysis to contain 41 ppm total ionic and coordinate bromine.

COMPARATIVE EXAMPLE III

Five grams of the 58 ppm bromine contaminated concentrated acetic acid are charged to a Fisher-Porter Bottle together with 5.0 grams of 4×8 mesh (U.S. Standard Sieve) Pd/C particulate catalyst having a Pd crystallite content of 0.5 weight percent on 1100 $m^2/g$ surface area to mass activated carbon. The bottle is charged with hydrogen to a gauge pressure of 1.75 $kg/cm^2$ and heated by a water bath to 100° C. for 2 hours while the bottle's contents are stirred. The acetic acid so treated is separated from the catalyst and is analyzed by X-ray diffraction. The recovered acetic acid is found to contain 20 ppm total ionic and coordinate bromine.

ILLUSTRATIVE EXAMPLES 1 AND 2

The process of Comparative Example III is repeated. After the 2 hours of stirring the acetic acid is separated from the Pd/C catalyst and divided into two equal volume portions. The first portion is percolated through 1.0 gram of activated alumina and is found by X-ray diffraction to contain thereafter less than 3 ppm total ionic and coordinate bromine. The second portion is percolated through the low metal content activated carbon described in Comparative Example II and is found by X-ray diffraction analysis thereafter to contain less than 3 ppm total ionic and coordinate bromine.

The amount of Pd/C catalyst and the solid absorbants used in Illustrative Examples 1 and 2 are not the optimum with respect to the quantity of acetic acid therein used. However, one of ordinary skill in this art can readily determine the optimum Pd/C catalyst and absorbant to use per unit weight or volume of bromine contaminated concentrated acetic acid relative to the amount of total bromine contaminant therein to achieve the benefits of this invention as exemplified above.

The invention claimed is:

1. The method of removing bromine from acetic acid of 95 to 100 weight percent concentration contaminated with ionic and co-ordinate bromine in a total amount of from 0.0005 to 0.015 weight percent by contacting hydrogen and said contaminated acetic acid with a palladium catalyst having Pd crystallites dispersed on the surface of low extraneous metal content activated carbon having a surface area to unit mass ratio of at least 800 $m^2/g$, separating the acetic acid from the catalyst, contacting the separated acetic acid with a solid absorbant, and separating acetic acid from the absorbant.

2. The method of claim 1 wherein the palladium catalyst is contacted with the contaminated acetic acid in the vapor phase and the absorbant is contacted with a vapor phase of acetic acid.

3. The method of claim 1 wherein the palladium catalyst in particulate form is contacted with the contaminated acetic acid in the liquid phase and thereafter the liquid acetic acid is contacted with particulate solid absorbant.

4. The method of claim 3 wherein the palladium catalyst contains 0.5 weight percent palladium and the solid absorbant is activated alumina.

5. The method of claim 3 wherein the palladium catalyst contains 0.5 weight percent palladium and the solid absorbant is low metal content activated carbon.

* * * * *